US00PP12796P2

(12) United States Plant Patent
Kanno

(10) Patent No.: US PP12,796 P2
(45) Date of Patent: Jul. 23, 2002

(54) OSTEOSPERMUM PLANT NAMED 'KAKEGAWA AU1'

(75) Inventor: Masao Kanno, Chigasaki (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/657,539

(22) Filed: Sep. 8, 2000

(51) Int. Cl.[7] ..... A01H 5/00

(52) U.S. Cl. ..... Plt./360

(58) Field of Search ..... Plt./360

*Primary Examiner*—Bruce R. Campell
*Assistant Examiner*—Annette Para
(74) *Attorney, Agent, or Firm*—Rothwell, Figg, Ernst & Manbeck

(57) ABSTRACT

The present invention relates to a new and distinct variety of *Osteospermum fruticosum* (L.) Norl plant named 'Kakegawa AU1'. This new plant has a suitable form for pot culture and also possesses large white flowers that stay open into the evening hours or under low light conditions.

1 Drawing Sheet

BACKGROUND OF THE INVENTION

The present invention relates to a new and distinct variety of the Compositae family. The new variety, a member of the species *Osteospermum fruticosum* (L.) Norl., named 'Kakegawa AU1'. This species is one of several species of Osteospermum that are commonly referred to as Cape Daisy.

The new variety originated as a first generation hybrid seedling from a controlled hybridization. This hybridization was done in 1991, at the Sakata Seed Corporation, Chogo Research Station in Chogo Prefecture, Japan. The objective of this breeding program was to develop plants with suitable form for pot culture that also possessed large flowers that would stay open into the evening hours. The flowers of *Osteospermum fruticosum* (L.) Norl. usually close under low light conditions, such as in the evening.

The original parent lines for the new variety were *Osteospermum fruticosum* (L.) Norl. breeding lines 474 and 247, female and male respectively. From this hybridization one hundred first generation seedlings were obtained and grown to mature, flowering plants. Five of these new plant lines were selected in 1992 for asexual reproduction and further evaluation. Each of these varieties possessed white or off white colored flower petals and flowers that remained open into the evening. In 1993, three of these lines were selected and evaluated due to their compact, funnel shaped plant habit and profuse branching and flowering. In 1995, one line was selected as 'Kakegawa AU1'. Further evaluation by the inventor during 1996 and 1997 demonstrated that the new variety's characteristics were firmly fixed and stable. Since this time the new variety has been trialed and vegetatively propagated at the assignee's facilities in Salinas, Calif. The new variety has been stable and fixed in this environment also.

The new variety has been observed under greenhouse and outdoor conditions in California and Japan. The phenotype of the new plant may vary somewhat with variations in temperature, day length, light intensity or soil media conditions. The observations noted below have been made using multiple 8 month old plants grown in Salinas, Calif. under the following conditions. Shoot tips were rooted in soil plug trays in August. After developing a root ball the plants were transplanted into six-inch diameter pots and grown outdoors through the winter to provide vernalization for flowering. In December, buds were pinched off to promote branching. Winter night temperatures averaged 40 to 50 degrees Fahrenheit. By May of the following year the plants were in full bloom. Average summer daytime temperatures in Salinas range from 60 to 75 degrees Fahrenheit depending on the month and the amount of coastal marine layer cloud cover.

BRIEF DESCRIPTION OF THE PHOTOGRAPHS

The accompanying color photographs illustrate the appearance the new variety, 'Kakegawa AU1'. The colors represented as true as possible using conventional photographic procedures.

DETAILED DESCRIPTION OF THE NEW VARIETY

Figure 1:
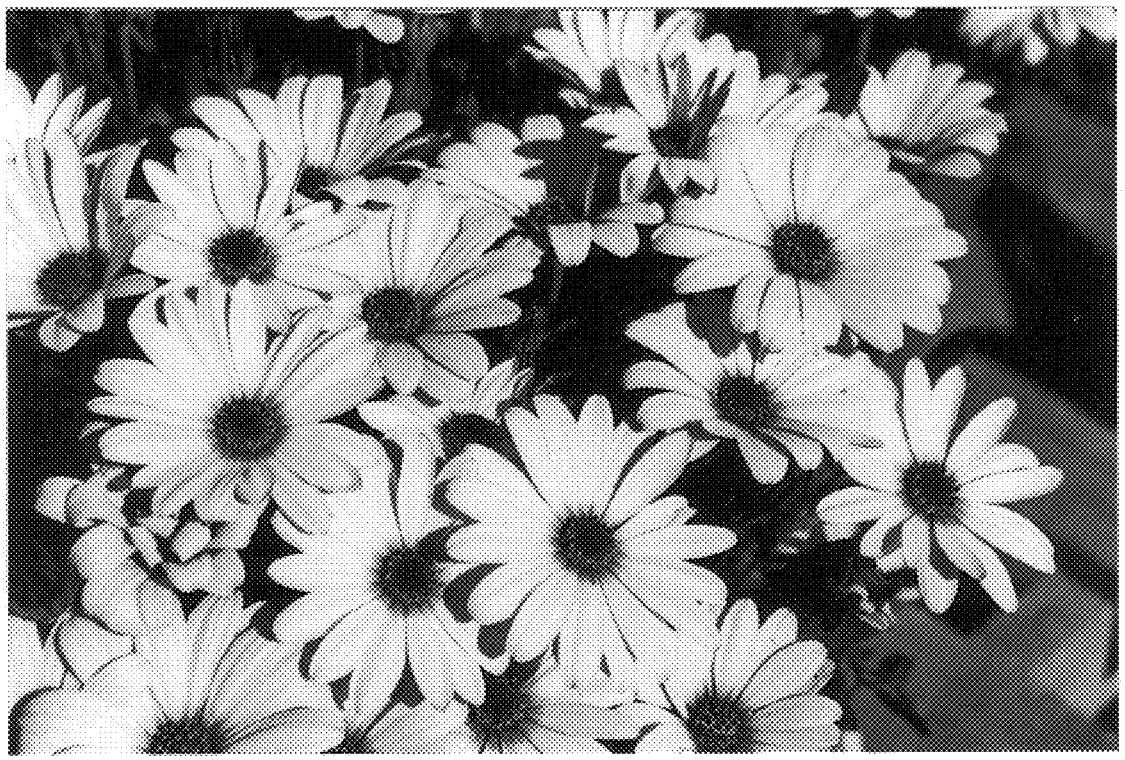
FIG. 1 is a close-up view of multiple blooms illustrating the petal and petal base colors.
Figure 2:
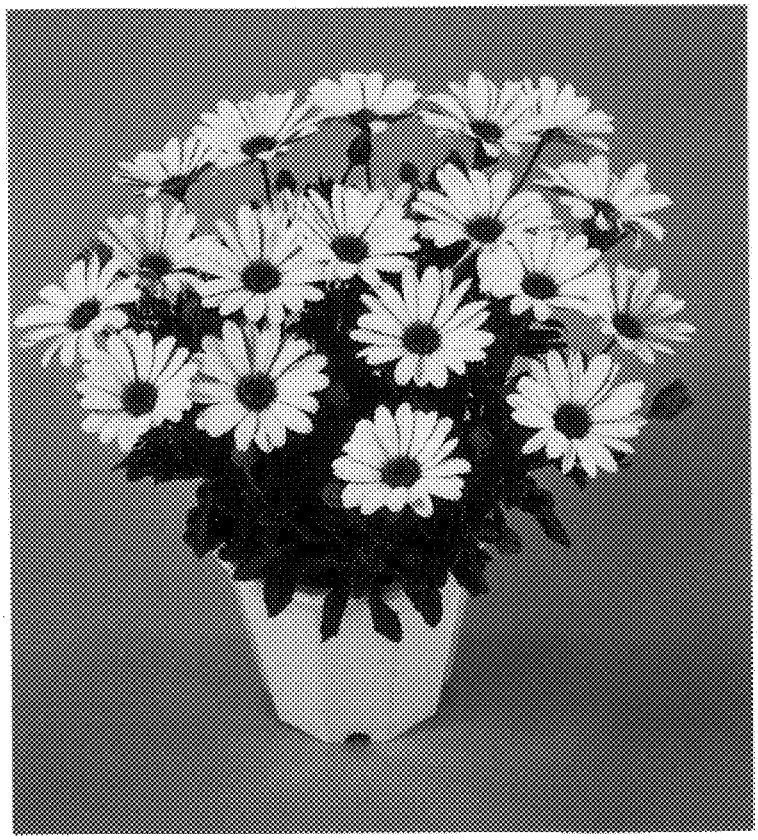
FIG. 2 is a view of the entire plant showing its form in pot culture when in full bloom.

The following traits and characteristics describe the new variety. Color references are made to The Royal Horticultural Society Colour Chart (R.H.S.), published by The Royal Horticultural Society of London, England, except where general terms of ordinary significance are used.

Classification:
- *Family.*—Compositae (Asteraceae).
- *Genus and species.*—*Osteospermum fruticosum* (L.) Norl.
- *Common names.*—African Daisy, Cape Daisy, Freeway Daisy.
- *Cultivar name.*—'Kakegawa AU1'.

Parentage:
- *Female parent.*—Line 474 (not patented).
- *Male parent.*—Line 247 (not patented).

Growth:
- *Habit.*—Vigorous, well branched.
- *Life cycle.*—Perennial.

Plant description:
- *Height.*—36 cm to 40 cm.
- *Width.*—40 cm to 50 cm.

*Form.*—Upright.
*Lastingness of florescence.*—7 days.

Stems:
*Stem color.*—RHS 144A (yellow-green).
*Stem description.*—Strong, erect, herbaceous, glabrous.
*Stem diameter.*—3 mm to 4 mm.
*Internode length.*—0.8 cm to 1.0 cm.

Leaves:
*Leaf arrangement.*—Alternate; sessile.
*Leaf apex.*—Mucronate.
*Leaf base.*—Oblique.
*Leaf color.*—Upper RHS 137A (green); lower RHS 137D (green).
*Leaf edge.*—Slightly serrated.
*Leaf shape.*—Lanceolate.
*Leaf venation.*—Pinnate.

Flowers:
*Phyllaries.*—Arrangement—symmetrical; length 10 mm; width 2 mm; shape linear; apex acute; margin entire; texture pubescent; upper color RHS 137D (green); lower color RHS 138C (green).
*Corolla.*—Free.
*Flower diameter.*—7.3 cm.
*Flowering habit.*—Determinate.
*Fragrance.*—None.
*Infloresence type.*—Solitary on terminal peduncles.
*Ovary.*—Inferior.
*Peduncle.*—Texture pubescent; length 4–6 cm; diameter 0.2 cm; color RHS 143C (green).
*Bud.*—Shape round, pointed at the top; length 1 cm; width 1 cm; color RHS 143C (green).
*Ray floret shape.*—Spatulate; apex obtuse; margin entire.
*Ray floret color.*—Dorsal surface of ray florets are RHS 155D white with RHS 70A (red-purple) base; ventral surface of ray florets is RHS 71A (red-purple); disk florets is RHS 89C (violet-purple).
*Ray floret size.*—3.5 cm to 4.5 cm in length.
*Ray floret number.*—17.
*Disc floret shape.*—Tubular.
*Disc floret size.*—5.0×0.5 mm.
*Disc floret number.*—55 per head.
*Propagation to bloom.*—18 to 20 weeks when rooted vegetative cuttings are transferred to a six-inch diameter pot in late Fall and given several weeks of below 50 degree Fahrenheit temperature prior to increasingly warmer spring weather.

Reproductive organ:
*Stigma.*—RHS N92 (violet-blue).
*Style.*—RHS 155D (white).
*Anther.*—RHS N92 (violet-blue).
*Filament.*—RHS 155D (white).
*Pollen color.*—RHS 23B (yellow-orange).
*Fruit and seed.*—Not produced.

DISEASE AND INSECT RESISTANCE

No known susceptibility to diseases or insects have been observed to date.

COMPARISON WITH OTHER KNOW VARIETIES

The closest known variety to 'Kakegawa AU1' is the variety 'Brightside', a plant described and illustrated in U.S. Plant Pat. No. 10,596. The following table compares the differences that distinguish the new variety from the similar variety 'Brightside'.

| Characteristic | 'Kakegawa AU1' | 'Brightside' |
|---|---|---|
| Flower diameter (cm) | 7.3 | 5.7 |
| Ray floret color (dorsal) | RHS 155 D white with RHS 70A (red-purple) base | Pure white |
| Ray floret color (ventral) | RHS 71A (red-purple) | RHS 90B (violet-blue) |

I claim:

1. A new and distinct plant of the Compositae family, *Osteospermum fruticosum* (L.) Norl., herein referred to by the name 'Kakegawa AU1', as illustrated and described.

* * * * *